United States Patent
Yu et al.

(10) Patent No.: US 8,535,248 B2
(45) Date of Patent: Sep. 17, 2013

(54) ULTRASONIC FAT REDUCTION AND BODY SHAPING MACHINE

(75) Inventors: Jinsheng Yu, Beijing (CN); Xingbo Fei, Beijing (CN); Keming Jiang, Beijing (CN); Chunsheng Li, Beijing (CN)

(73) Assignee: Beijing 3H Medical Technology Co., Ltd., Beijing (CN)

( * ) Notice: Subject to any disclaimer, the term of this patent is extended or adjusted under 35 U.S.C. 154(b) by 0 days.

(21) Appl. No.: 13/256,093

(22) PCT Filed: Mar. 12, 2010

(86) PCT No.: PCT/CN2010/071022
§ 371 (c)(1),
(2), (4) Date: Sep. 12, 2011

(87) PCT Pub. No.: WO2010/102582
PCT Pub. Date: Sep. 16, 2010

(65) Prior Publication Data
US 2012/0010542 A1    Jan. 12, 2012

(30) Foreign Application Priority Data
Mar. 13, 2009    (CN) .......................... 2009 1 0079849

(51) Int. Cl.
*A61H 1/00* (2006.01)
(52) U.S. Cl.
USPC ............................................................ 601/2
(58) Field of Classification Search
USPC ............................................................ 601/2
See application file for complete search history.

(56) References Cited

U.S. PATENT DOCUMENTS

| 6,052,611 | A | * | 4/2000 | Yanof et al. ................... 600/429 |
| 6,524,250 | B1 | | 2/2003 | Weber et al. |
| 2005/0107702 | A1 | * | 5/2005 | He et al. ........................ 600/439 |
| 2005/0154431 | A1 | * | 7/2005 | Quistgaard et al. ............. 607/96 |
| 2006/0058647 | A1 | * | 3/2006 | Strommer et al. ............ 600/434 |
| 2006/0074313 | A1 | | 4/2006 | Slayton et al. |
| 2007/0239079 | A1 | * | 10/2007 | Manstein et al. ................. 601/2 |

(Continued)

FOREIGN PATENT DOCUMENTS

| CN | 1076627 C | 12/2001 |
| CN | 1132639 C | 12/2003 |

(Continued)

OTHER PUBLICATIONS

Written Opinion, dated Jun. 17, 2010, six pages.

(Continued)

*Primary Examiner* — Tse Chen
*Assistant Examiner* — Hien Nguyen
(74) *Attorney, Agent, or Firm* — Brouse McDowell; Heather M. Barnes

(57) ABSTRACT

The invention discloses an ultrasonic fat reduction and body shaping machine that includes a treatment head, a wave source carrying apparatus, a mechanical arm, a treatment bed, a lift cylinder body, a touch screen and control circuits. A menu for user selection operation is provided on the touch screen. The treatment head is clamped in the wave source carrying apparatus so as to be fixedly connected to the mechanical arm as a whole. The mechanical arm is fixedly connected to the lift cylinder body that is fastened on the treatment bed-base. The invention is to provide an ultrasonic fat reduction and body shaping machine that facilitates assembling and disassembling of a treatment head, elevates and descends a mechanical arm freely. The ultrasonic fat reduction and body shaping machine has an ultrasonic frequency of 1 MHz to 3 MHz using an ultrasonic emission mode with high intensity, narrow pulse width and low duty cycle.

5 Claims, 11 Drawing Sheets

(56) References Cited

U.S. PATENT DOCUMENTS

2012/0016239 A1* 1/2012 Barthe et al. .................. 600/439

FOREIGN PATENT DOCUMENTS

| | | |
|---|---|---|
| CN | 1662177 A | 8/2005 |
| CN | 1230120 C | 12/2005 |
| WO | 2010/102582 A1 | 9/2010 |

OTHER PUBLICATIONS

First Office Action issued in related Chinese application No. 200910079849.1; dated Jul. 6, 2011; four pages.

Second Office Action issued in related Chinese application No. 200910079849.1; dated Jul. 30, 2011; four pages.

International Preliminary Report on Patentability; dated Sep. 13, 2011; seven pages.

* cited by examiner

ULTRASONIC FAT REDUCTION AND BODY SHAPING MACHINE

TECHNICAL FIELD

This invention relates to a fat reduction and body shaping machine, and in particular, to an ultrasonic fat reduction and body shaping machine.

BACKGROUND ART

Recently, a novel ultrasonic fat reduction technology emerges in the world. A focused ultrasonic wave with a frequency of about 500 kHz is continuously transmitted to a patient transcutaneously via a hand-held ultrasonic transducer. The ultrasonic wave passes through the skin and reaches the underlying adipose layer. The structure of fat cells is destroyed by the physical effects such as thermal effect, high sound pressure due to the ultrasonic wave, so as to free the lipid contents included therein. The free lipid, after a period of time, is absorbed via the body's own metabolism, thereby to achieve a fat reduction and body shaping effect. However, the speed of treatment is restrained because the aforementioned hand-held ultrasonic transducer is operated with great complexity and effort, and inconvenient to assemble and disassemble a treatment head.

SUMMARY OF INVENTION

The objective of this invention is to provide an ultrasonic fat reduction and body shaping machine that can be operated easily and conveniently, saves operator's labor, facilitates assembling and disassembling of a treatment head, elevates and descends a mechanical arm freely, thus providing a rapid treatment speed. The ultrasonic fat reduction and body shaping machine has an ultrasonic frequency of 1 MHz to 3 MHz using an ultrasonic emission mode with high intensity, narrow pulse width and low duty cycle.

The technical solution of the ultrasonic fat reduction and body shaping machine of this invention is described as below.

The ultrasonic fat reduction and body shaping machine of this invention comprises a treatment head, a wave source carrying apparatus, a mechanical arm, a treatment bed-top, a lift cylinder body, a treatment bed-base, a touch screen, a button, and control circuits. A menu for user selection operation is provided on the touch screen. The button is a switch for controlling up-and-down movement of the lift cylinder body. The treatment head is clamped in the wave source carrying apparatus so as to be fixedly connected to the mechanical arm as a whole. The mechanical arm is fixedly connected to the lift cylinder body that is fastened on the treatment bed-base.

The main part of the treatment head contains a self-focusing spherical ultrasonic transducer. The ultrasound energy converges to a focus via the focusing ceramic plate. The internal structure of the treatment head further includes an ultrasonic wave transmission medium-container and a circulating water cooling system. The external structure of the main part of the treatment head includes a handle for the treatment head and an adapter. The handle for the treatment head can be hand-held or machine-mountable so that the treatment head can be used under a manual treatment mode or an automatic treatment mode.

The mechanical arm includes hold parts, a mounting seat for the treatment head, parallelogram connecting rods, a locking member, a rotary shaft, an air spring, and a connector. The hold parts, both in a rod shape, are located one at each side of the mounting seat for the treatment head respectively and movably connected thereto. The mounting seat for the treatment head is a connector between the mechanical arm and the wave source carrying apparatus. One side of the mounting seat for the treatment head is fixedly connected to the parallelogram connecting rods and the other side of which is fixedly connected to the wave source carrying apparatus. There are two parallelogram connecting rods that are connected together via a trapezoidal connector. One of the parallelogram connecting rods is connected at one end to the trapezoidal connector via the rotary shaft, and fixedly connected at the other end to the mounting seat for the treatment head. The other of the parallelogram connecting rods is fixedly connected at one end to the trapezoidal connector, and movably connected at the other end to a triangular connector via the rotary shaft. The parallelogram connecting rods can rotate freely about the rotary shaft. There are two air springs. One of the air springs is connected at one end to the trapezoidal connector via the rotary shaft, and connected at the other end with the locking member and fixedly connected to the mounting seat for the treatment head. The air spring is connected to the hold parts via a metal wire. The other of the air springs is connected at one end with the locking member and fixedly connected to the trapezoidal connector, and connected at the other end to the triangular connector via the rotary shaft. Rotating the hold parts respectively can rotate the mechanical arm about the rotary shaft. The hold parts drive the locking member to press the braking mechanism of the air spring, releasing the air spring from its locking state to move freely. Such combinational movements make the mechanical arm reach the position desired for the treatment. Moreover, by releasing the hold parts, the air spring can be tightly locked so as to self-lock to its position. The mounting seat for the treatment head is used for fastening the treatment head. Because the mechanical arm is a parallelogram connecting rod, and a mechanical arm bracket that is fixed on the lift cylinder body is parallel to the ground, it ensures that the treatment head is vertical to the ground.

The treatment bed includes a bed-top and a bed-base. The main frame of the bed-top is welded by metal pipes. Two groups of guide track-slider mechanisms and displacement driving mechanisms are provided along a length direction and a width direction of the treatment bed-top, respectively. Each group of the guide track-slider mechanisms has two guide tracks parallel to each other, and the two groups of the guide track-slider mechanisms are superposed orthogonally in direction. The treatment bed-base is a supporting structure that is welded by metal pipes for supporting the treatment bed. The control circuits for controlling the ultrasonic fat reduction and body shaping machine of this invention are installed between the treatment bed-top and bed-base. The guide track-slider mechanism can be driven by the displacement driving mechanism so that the treatment bed-top can move along the length direction and the width direction independently and respectively. The displacement driving mechanism is an electric motor.

The lift cylinder body includes an electric motor, a feed rod, a locking means and a mechanical arm bracket. The feed rod is a rod-shaped structure with high surface smoothness. The locking means has a central hole for the feed rod to be socketed thereinto. The mechanical arm bracket is a platform parallel to the ground. The feed rod and the locking means are socketed together and fixedly connected with each other. The lift cylinder body is fixedly connected to the locking means in a locking manner, and fixedly connected to the supporting structure of the treatment bed-base by means of the feed rod and the locking means. The mechanical arm bracket is fixedly connected to the triangular connector of the mechanical arm.

Inside the lift cylinder body is provided with a lift rod, and the lift cylinder body can make up-and-down movement driven by the electric motor.

The control circuits include a control circuit for the treatment head, a control circuit for the bed side of the treatment bed and a control circuit for the touch screen.

The control circuit for the treatment head includes the following modules:

a signal generation module which includes a chip AD9834 and its peripheral circuit, and which can produce a high-frequency sine wave signal by inputting data at a control terminal of the signal generation module;

a signal conversion module which includes a chip MAX913 and its peripheral circuit, and which can convert the high-frequency sine wave signal to a high-frequency digital signal;

a posterior stage interference reduction module which includes a chip 74HC04 and its peripheral circuit, and which can reduce the posterior stage interference of the following signals by using inversion cancellation means: the high-frequency digital signal, a PWM signal and high-frequency signals 1Q and 1Q#;

a signal control module which includes a chip SN74HC74 and its peripheral circuit, and which can convert the high-frequency digital signal to a high-frequency digital signal having the same duty cycle as the PWM signal, wherein the PWM signal, the posterior stage interference of which is reduced by using the inverting function of the posterior stage interference reduction module, is inputted into the signal control module so as to control the width of two narrow pulses, and thereby to adjust the duty cycle of the high-frequency signals 1Q and 1Q#;

a signal delay module which includes a chip DS1013 and its peripheral circuit, and which can delay and output the high-frequency signals 1Q and 1Q#, the posterior stage interference of which is reduced by the posterior stage interference reduction module twice, so as to obtain two high-frequency signals which differ from each other by half a cycle;

a signal computation module which includes a chip 74HC08 and its peripheral circuit, and which can make an "AND" operation on the following signals so as to produce four signals: (1) two high-frequency signals which differ from each other by half a cycle, (2) a signal from positive power source, and (3) the PWM signals outputted by the signal control module and the high-frequency digital signals having the same duty cycle as the PWM signals; and a signal amplification and transmission module, which includes a chip IXDD414 and its peripheral circuit, and which can amplifies the four signals and output the amplified four signals to an ultrasonic transmitting apparatus.

The ultrasonic fat reduction and body shaping machine of this invention has the following benefits:

Due to the introduction of the wave source carrying apparatus, the treatment head of the ultrasonic fat reduction and body shaping machine of the invention can be adapted to different body sites of a patient, so that an operator can operate the machine conveniently and easily, assemble and disassemble the treatment head conveniently.

Due to the existence of the lift mechanism and lift cylinder body, the mechanical arm of the ultrasonic fat reduction and body shaping machine of the invention can be elevated and descended freely using the electric motor driving mechanism.

The treatment bed of the ultrasonic fat reduction and body shaping machine of the invention can move along the length direction and width direction of the bed side independently and respectively, and thereby can increase the treatment speed.

The control circuits for the treatment head of the ultrasonic fat reduction and body shaping machine can increase the ultrasound working frequency up to 1 to 3 MHz, producing obviously less influence on the deep tissues of a human body than that of a 500 kHz ultrasound. In other words, the ultrasonic wave having a frequency of 1 to 3 MHz obviously has much improved safety when being used for the fat reduction treatment.

The control circuits for the treatment head of the ultrasonic fat reduction and body shaping machine can produce high intensity ultrasound. Meanwhile, the ultrasonic emission mode has a narrow pulse width and a low duty cycle. The high sound pressure produced by the high-intensity ultrasound strengthens the destructive effect on the fat cell structure. The emission mode with a narrow pulse width and a low duty cycle reduces the tissue temperature elevation caused by the ultrasound energy, enhances the destruction selectiveness due to the ultrasound energy. Therefore, it is useful and helpful for reducing the side effects and improving the efficiency of the treatment.

Figure 1:
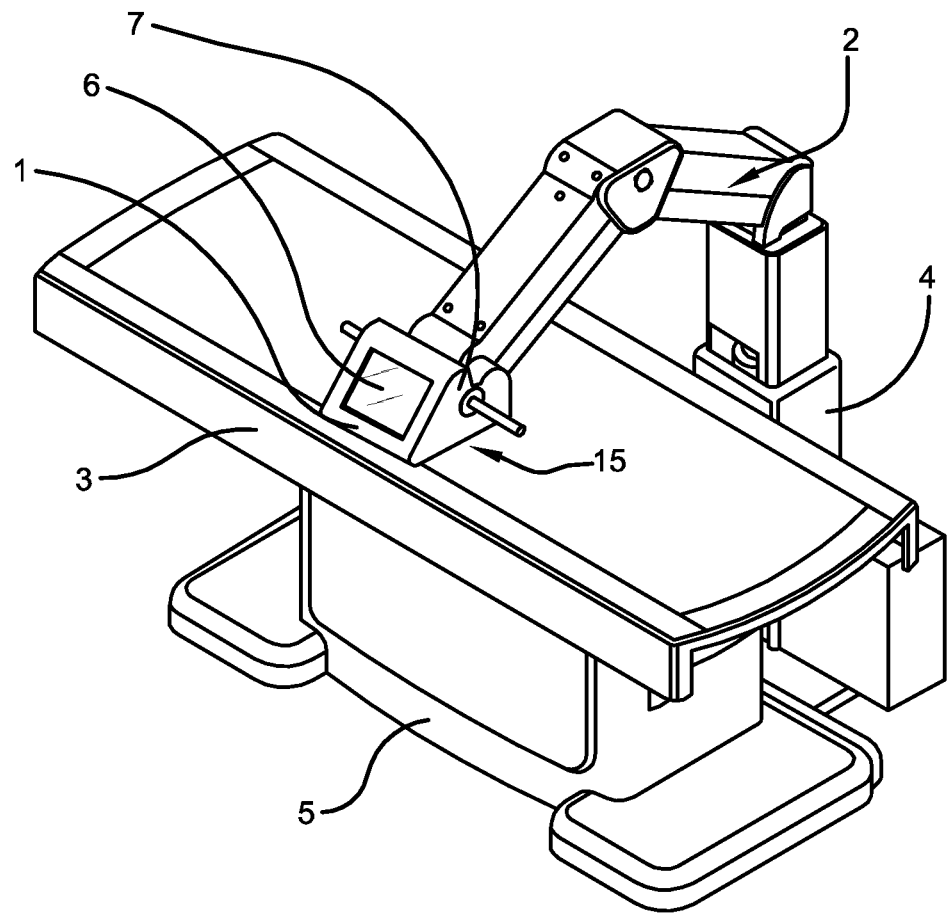
FIG. 1 is a schematic view showing the external structure of the ultrasonic fat reduction and body shaping machine of this invention as a whole machine.
Figure 2:
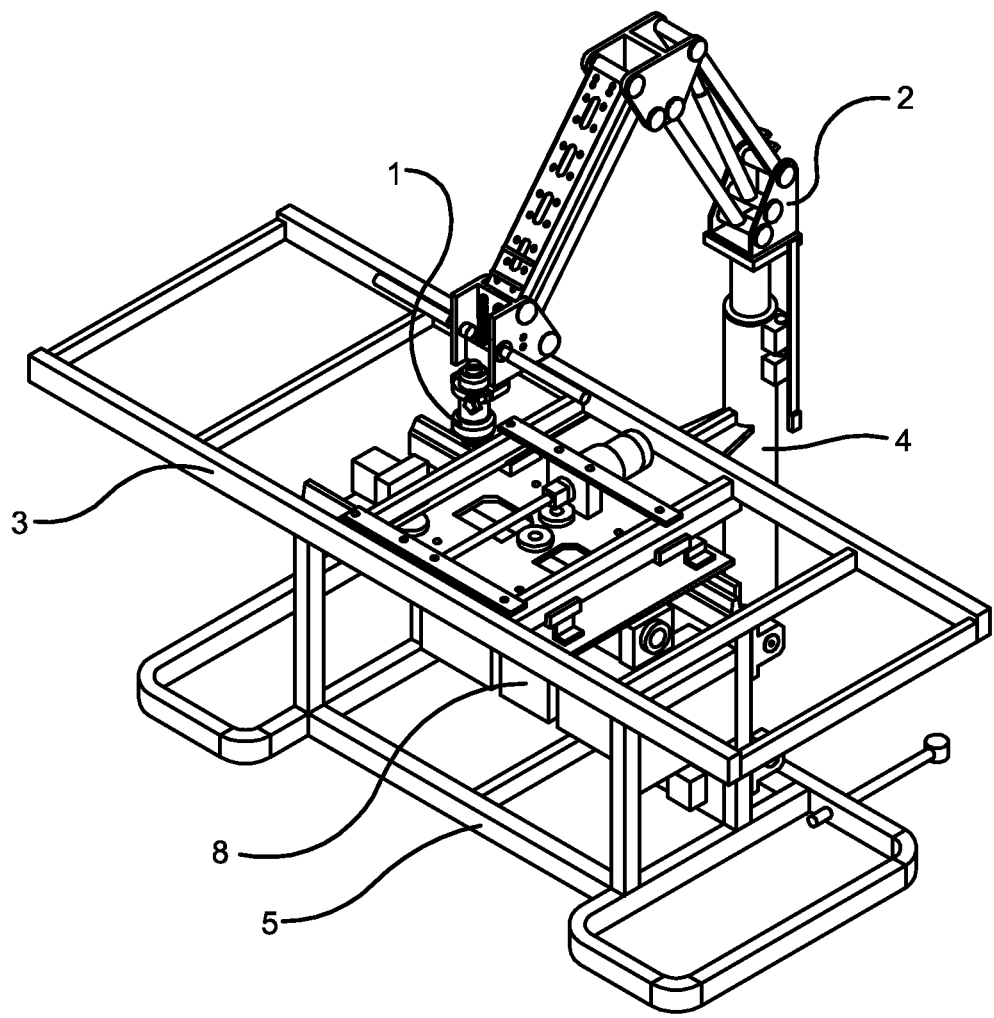
FIG. 2 is a schematic view showing the internal structure of the ultrasonic fat reduction and body shaping machine of this invention as a whole machine.

REFERENCE SIGNS IN THE DRAWINGS 1 treatment head; 2 mechanical arm; 3 treatment bed-top; 4 lift cylinder body; 5 treatment bed-base; 6 touch screen; 7 button; 8 control circuit; 9 handle for the treatment head; 10 adapter; 11 self-focusing spherical ultrasonic transducer; 12 ultrasonic transmission medium container; 13 circulating water cooling system; 14 focusing ceramic plate; 15 wave source carrying apparatus; 16 hold parts; 17 mounting seat for the treatment head; 18 air spring; 19 parallelogram connecting rods; 20 locking member; 21 rotary shaft; 22 guide track; 23 slider; 24 electric motor; 25 feed rod; 26 locking means; 27 mechanical arm bracket; and 28 lift rod.

PREFERRED EMBODIMENTS

Referring to FIG. 1, an ultrasonic fat reduction and body shaping machine of this invention comprises a treatment head 1, a mechanical arm 2, a treatment bed-top 3, a lift cylinder body 4, a treatment bed-base 5, a touch screen 6, a button 7, a control circuit 8 and a wave source carrying apparatus 15. A menu for user selection operation is provided on the touch screen 6. The button 7 is a switch for controlling up-and-down motion of the lift cylinder body 4. The treatment head 1 is clamped in the wave source carrying apparatus 15 so as to be fixedly connected to the mechanical arm 2 as a whole. The mechanical arm 2 is fixedly connected to the lift cylinder body 4 which is fastened on the treatment bed-base 5.

Figure 3:
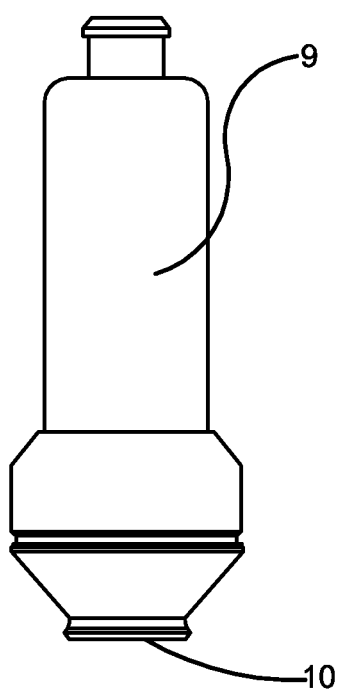
FIG. 3 is a schematic view showing the external structure of the treatment head of the ultrasonic fat reduction and body shaping machine of this invention.
Figure 4:
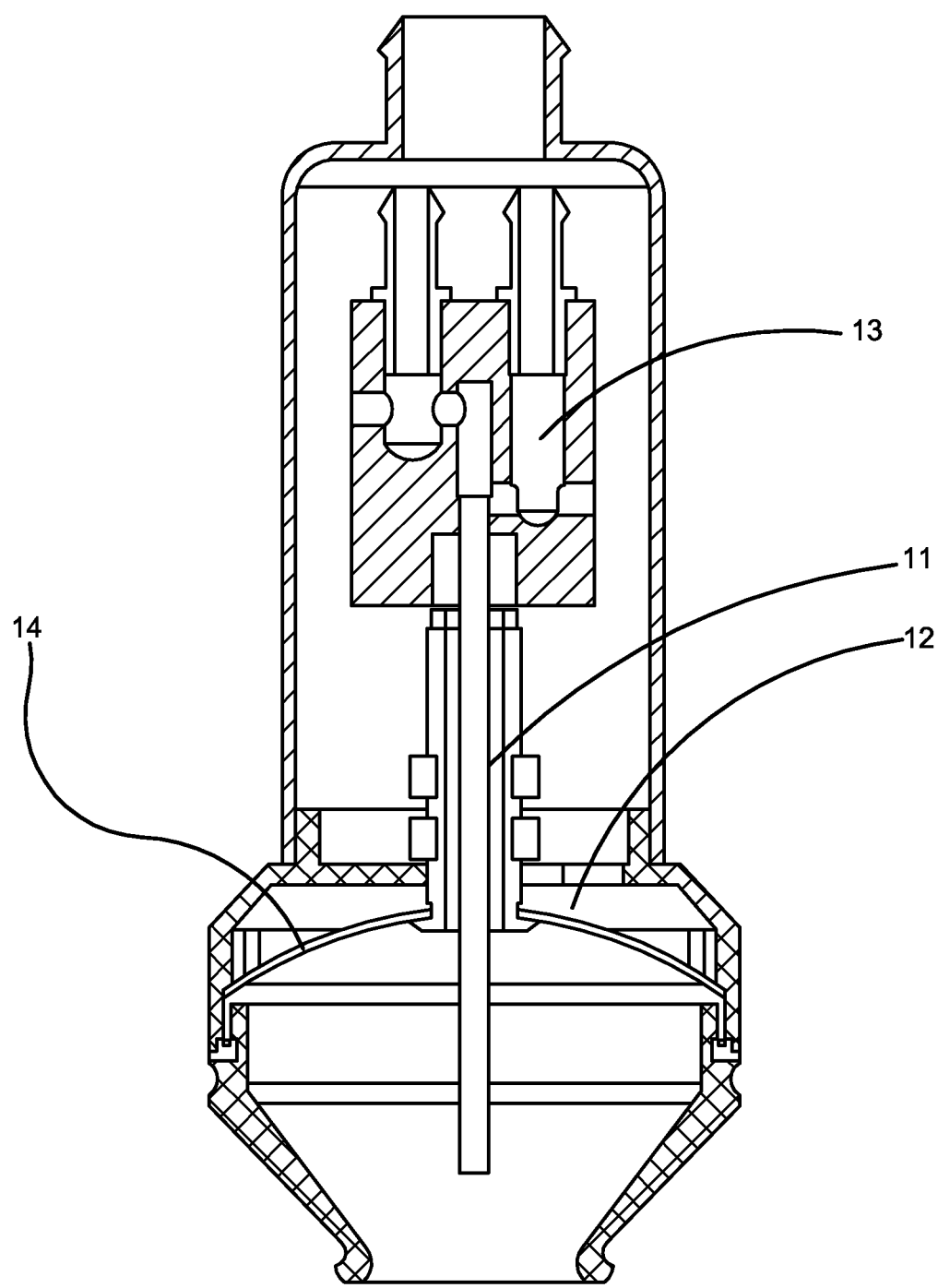
FIG. 4 is a sectional view showing the treatment head of the ultrasonic fat reduction and body shaping machine of this invention.

Referring to FIGS. 3 and 4, the main part of the treatment head 1 is configured as a self-focusing spherical ultrasonic transducer 11. The ultrasonic energy converges to a focus via the focusing ceramic plate 14. The internal structure of the treatment head 1 further includes an ultrasonic transmission medium container 12 and a circulating water cooling system 13. The external structure of the main part of the treatment head 1 includes a handle 9 for the treatment head and an adapter 10. The handle 9 for the treatment head may be hand-held or machine-mountable, so as to be used under a manual treatment mode and an automatic treatment mode of the treatment head 1.

Figure 5:
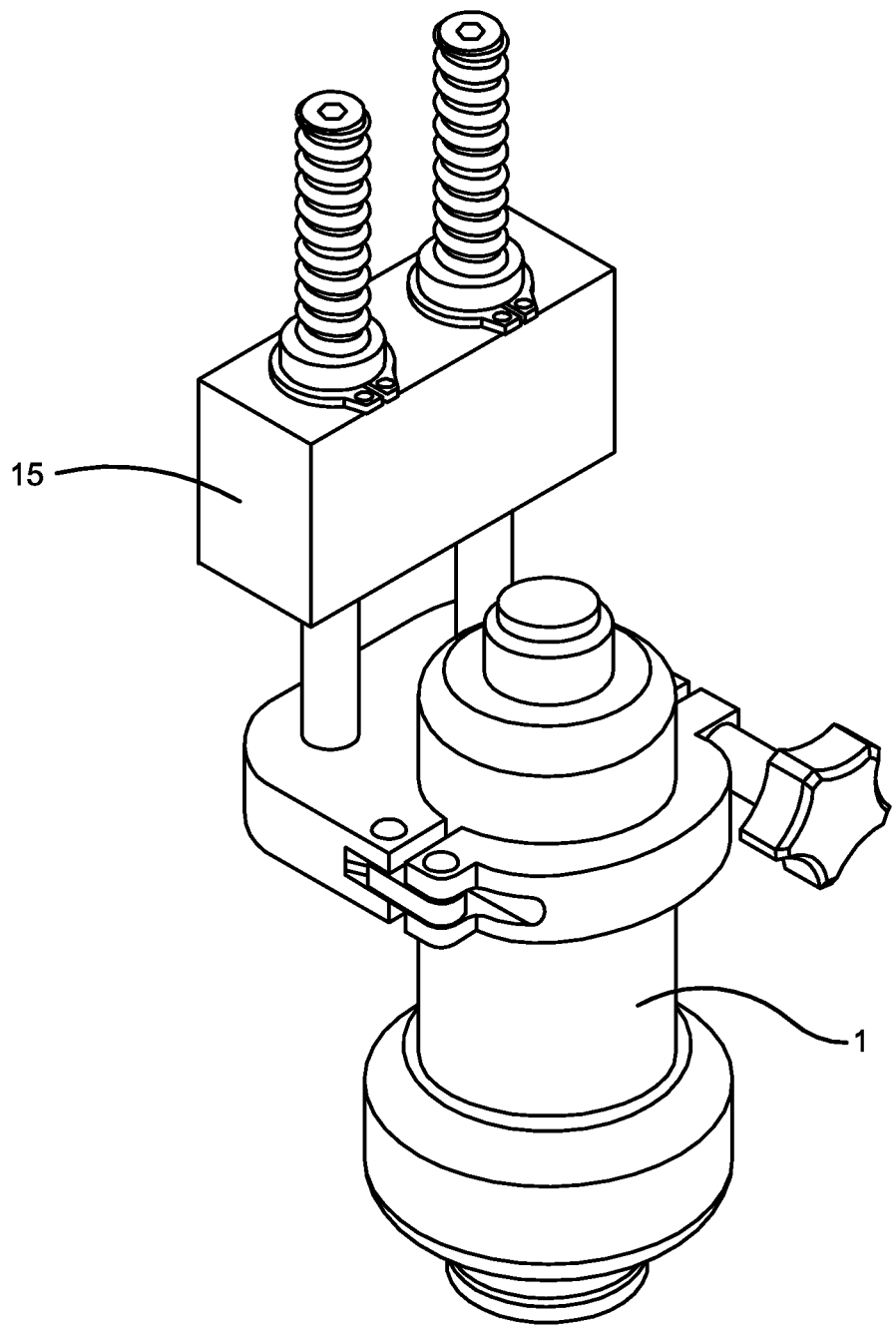
FIG. 5 is a schematic view showing the structure after the treatment head and the wave source carrying apparatus of the ultrasonic fat reduction and body shaping machine of this invention are connected to each other.
Figure 6:
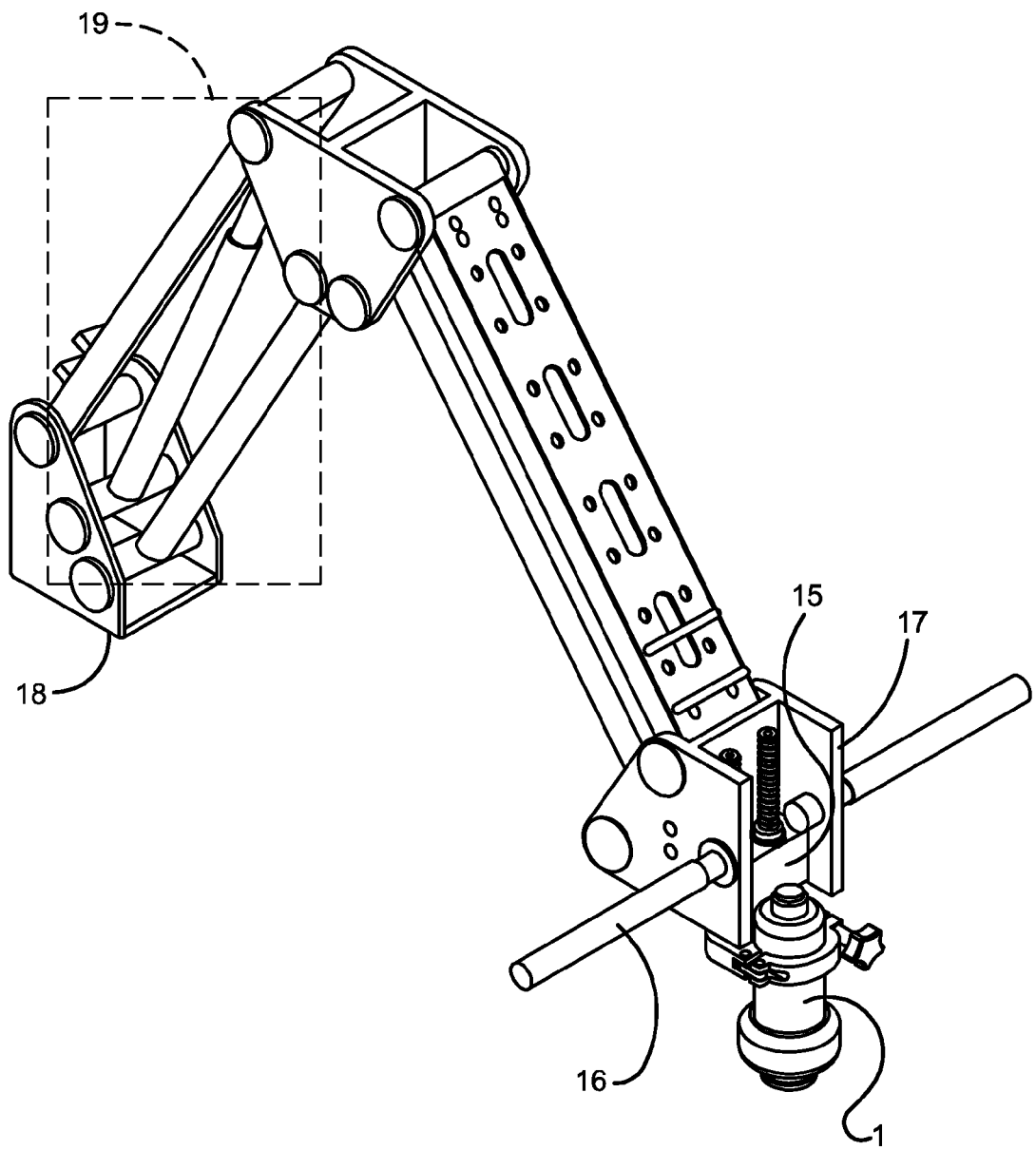
FIG. 6 is a schematic view showing the structure after the treatment head of the ultrasonic fat reduction and body shaping machine is clamped in the wave source carrying apparatus as a whole and then connected to the mechanical arm.

Referring to FIGS. 5 and 6, the treatment head is clamped in the wave source carrying apparatus 15, and they as a whole structure are fixedly connected to a mounting seat 17 of the treatment head of the mechanical arm 2.

Figure 7:
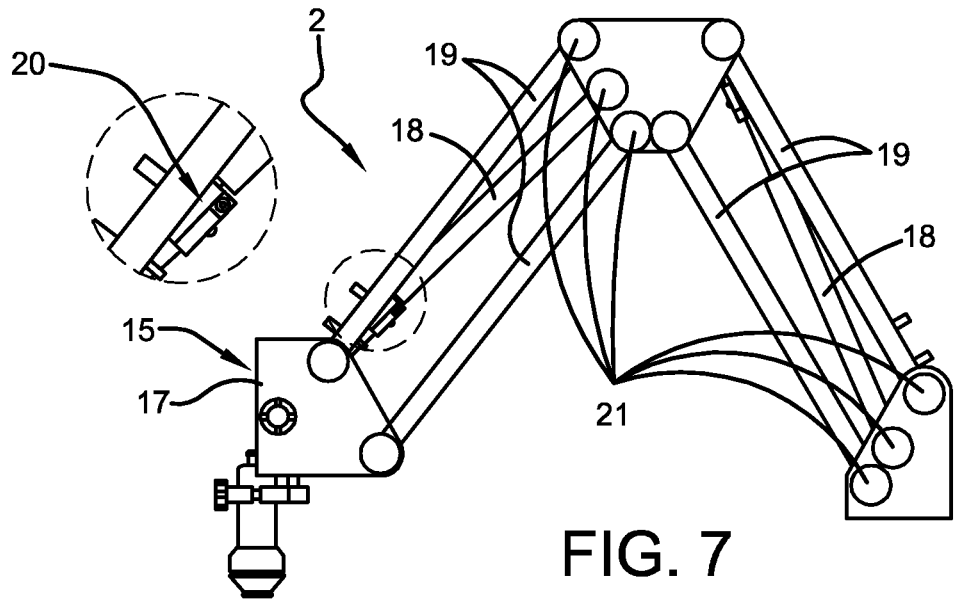
FIG. 7 is a schematic view showing the relative position of each unit of the mechanical arm of the ultrasonic fat reduction and body shaping machine of this invention.

Referring to FIGS. 6 and 7, the mechanical arm 2 includes hold parts 16, the mounting seat 17 for the treatment head, parallelogram connecting rods 19, a locking member 20, a rotary shaft 21 and air springs 18. The hold parts 16, each in a rod shape, are located one at each side of the mounting seat 17 of the treatment head respectively, and movably connected thereto. The mounting seat 17 for the treatment head is a connector for the mechanical arm 2 and the wave source carrying apparatus 15. One side of the mounting seat 17 for the treatment head is fixedly connected to the parallelogram connecting rod 19 and the other side of which is fixedly connected to the wave source carrying apparatus 15. There are two groups of parallelogram connecting rods 19, which are connected together via a trapezoidal connector. One group of the parallelogram connecting rods 19 is connected at one end to the trapezoidal connector via the rotary shaft 21, and fixedly connected at the other end to the mounting seat 17 for the treatment head. The other group of the parallelogram connecting rods 19 is fixedly connected at one end to the trapezoidal connector, and movably connected at the other end to a triangular connector via the rotary shaft 21. The parallelogram connecting rods 19 can rotate freely about the rotary shaft 21. There are two air springs 18. One of the air springs 18 is connected at one end to the trapezoidal connector via the rotary shaft 21, and connected at the other end with the locking member 20 and fixedly connected to the mounting seat 17 for the treatment head. This air spring 18 is connected to the hold parts 16 via a metal wire. The other of the air springs 18 is connected at one end with the locking member 20 and fixedly connected to the trapezoidal connector, and connected at the other end to the triangular connector via the rotary shaft 21. Rotating the hold parts 16 respectively can rotate the mechanical arm 2 about the rotary shaft 21. The hold parts 16 drive the locking member 20 to press a braking mechanism of the air spring 18, releasing the air spring from its locking state to move freely. Such combined movements makes the mechanical arm 2 reach the position desired for the treatment. Moreover, by releasing the hold parts 16, the air spring 18 can be tightly locked so as to self-lock to its position. The mounting seat 17 for the treatment head is used for fastening the treatment head. Because the mechanical arm 2 is a parallelogram connecting rod 19, and a mechanical arm bracket 29 that is fixed on the lift cylinder body 4 is parallel to the ground, it ensures that the treatment head 1 is vertical to the ground.

Figure 8:
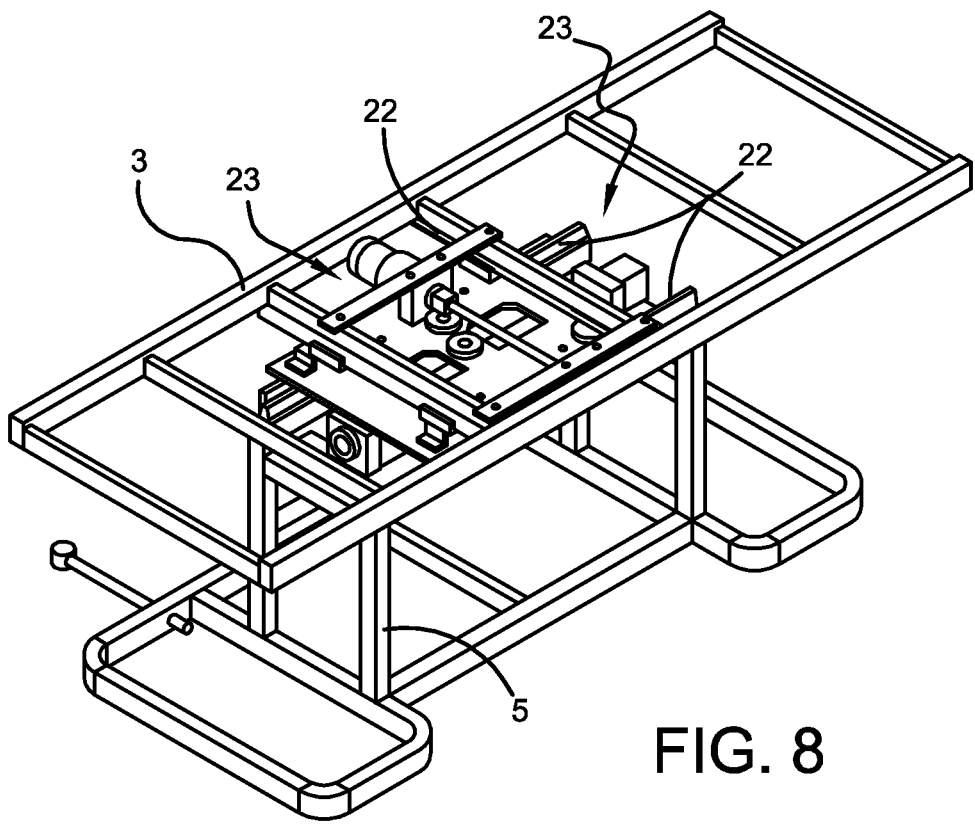
FIG. 8 is a schematic view showing the internal structure of the treatment bed of the ultrasonic fat reduction and body shaping machine of this invention.
Figure 9:
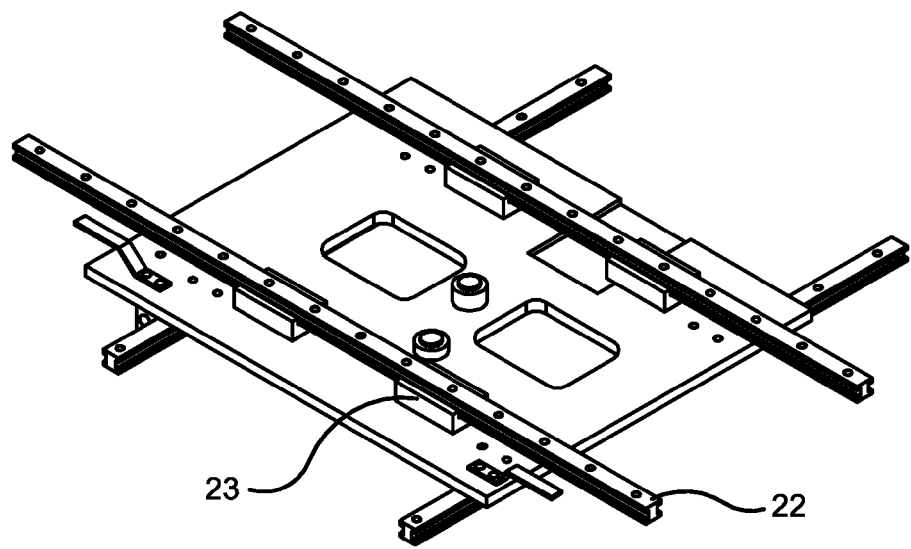
FIG. 9 is a schematic view showing the structure of the guide track track-slider mechanism of the ultrasonic fat reduction and body shaping machine of this invention.

Referring to FIGS. 8 and 9, the treatment bed includes a bed-top 3 and a bed-base 5. The main frame of the bed-top 3 is welded by metal pipes. Two groups of guide track 22-slider 23 mechanisms and displacement driving mechanisms are provided along a length direction and a width direction of the bed-top 3 of the treatment bed, respectively. Each group of the guide track 22-slider 23 mechanisms has two guide tracks parallel to each other, and the two groups of the guide track 22-slider 23 mechanisms are superposed orthogonally in direction. The treatment bed-base 5 is a supporting structure that is welded by metal pipes for supporting the treatment bed. The control circuits 8 for controlling the ultrasonic fat reduction and body shaping machine of this invention are installed between the treatment bed-top 3 and the bed-base 5. The guide track 22-slider 23 mechanism can be driven by the displacement driving mechanism so that the treatment bed-top 3 can move along the length direction and the width direction independently and respectively. The displacement driving mechanism is an electric motor.

Figure 10:
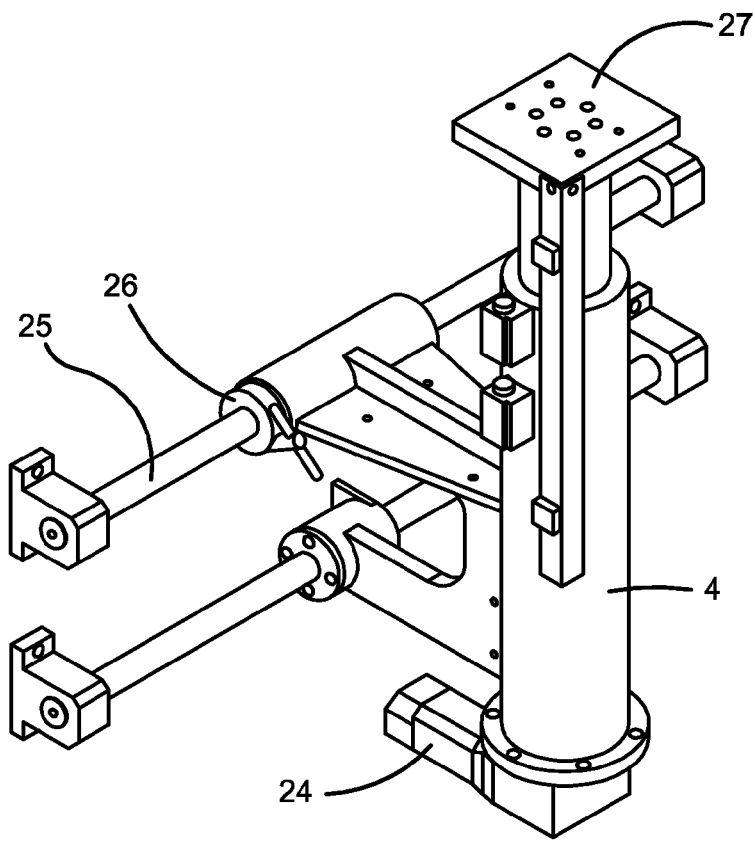
FIG. 10 is a schematic view showing the external structure of the lift cylinder body of the ultrasonic fat reduction and body shaping machine of this invention.
Figure 11:
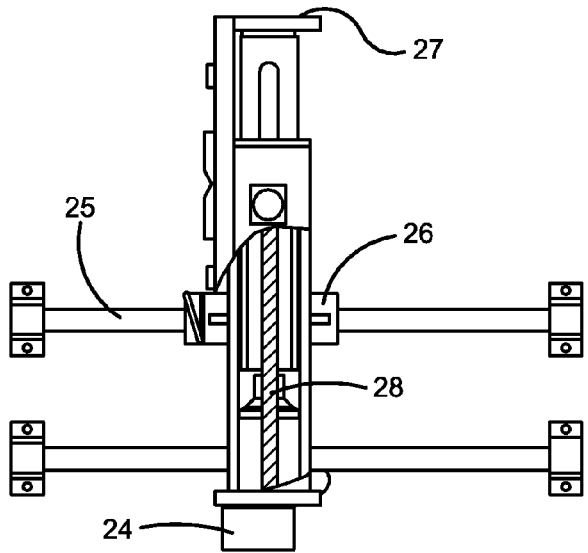
FIG. 11 is a sectional view showing a part of the lift cylinder body of the ultrasonic fat reduction and body shaping machine of this invention.
Figure 12:
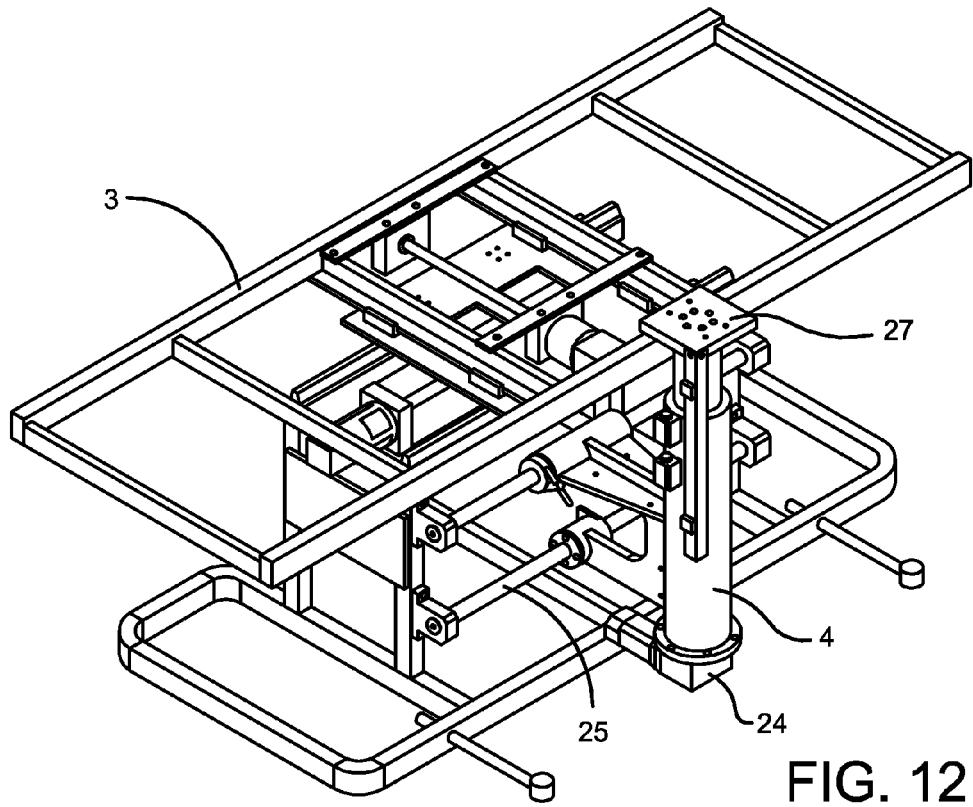
FIG. 12 is a schematic view showing the structure when the lift cylinder body is fixedly connected to the support structure of the treatment bed-base according to the ultrasonic fat reduction and body shaping machine of this invention.

Referring to FIG. 10, the lift cylinder body 4 includes an electric motor 24, a feed rod 25, a locking means 26 and a mechanical arm bracket 27. The feed rod 25 is a rod-shaped structure with high surface smoothness. The locking means 26 has a central hole for the feed rod 25 to be socketed thereinto. The mechanical arm bracket 27 is a platform parallel to the ground. The feed rod 25 and the locking means 26 are socketed together and fixedly connected with each other. The lift cylinder body 4 is fixedly connected to the locking means 26 in a locking manner, and, referring to FIG. 12, fixedly connected to the supporting structure of the treatment bed-base 5 by means of the feed rod 25 and the locking means 26. The mechanical arm bracket 27 is fixedly connected to the triangular connector of the mechanical arm 2. Referring to FIG. 11, inside the lift cylinder body 4 is provided with a lift rod 28 which is fixedly connected to the mechanical arm bracket 27, and the lift cylinder body 4 can make up-and-down movement driven by the electric motor 24.

Figure 13A:
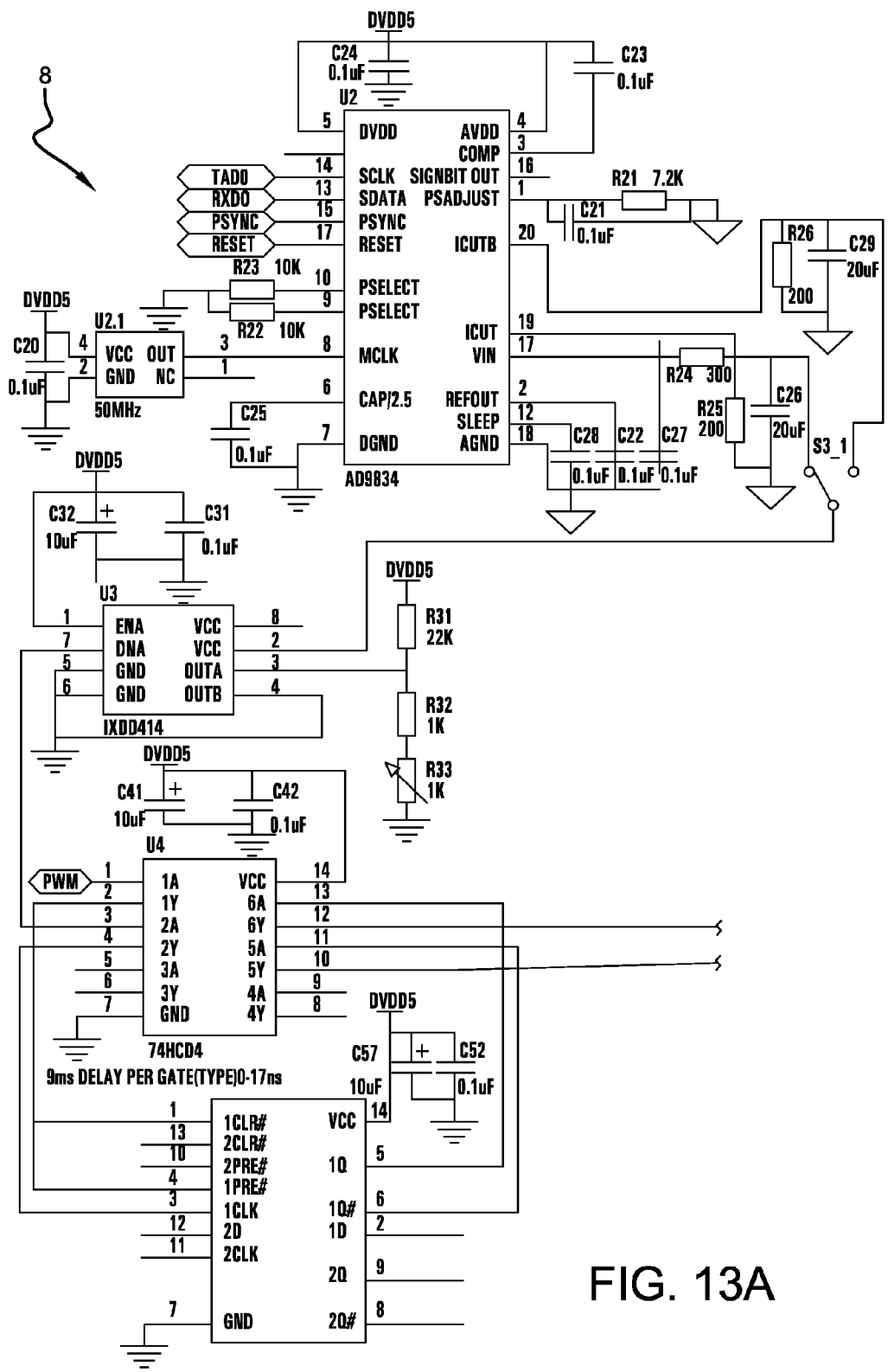
FIG. 13 is a schematic view showing the control circuit for the treatment head of the ultrasonic fat reduction and body shaping machine of this invention.
Figure 13B:
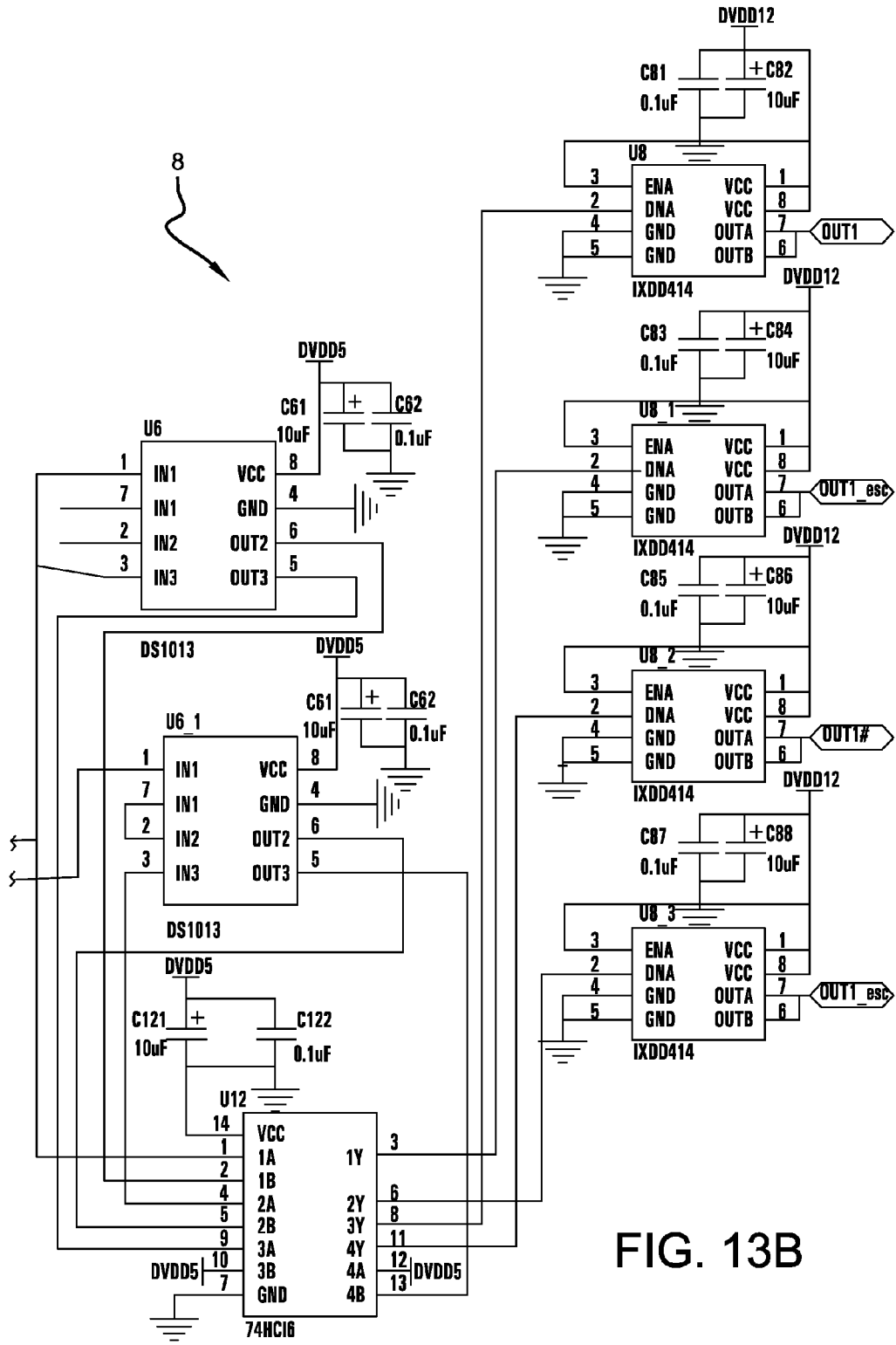

Referring to FIG. 13, the control circuits 8 include a control circuit for the treatment head, a control circuit for the bed side of the treatment bed and a control circuit for the touch screen.

The control circuit for the treatment head includes the following modules:

a signal generation module which includes a chip AD9834 and its peripheral circuit, and which can produce a high-frequency sine wave signal by inputting data at a control terminal of the signal generation module;

a signal conversion module which includes a chip MAX913 and its peripheral circuit, and which can convert the high-frequency sine wave signal to a high-frequency digital signal;

a posterior stage interference reduction module which includes a chip 74HC04 and its peripheral circuit, and which can reduce the posterior stage interference of the following signals by using inversion cancellation means: the high-frequency digital signal, a PWM signal and high-frequency signals 1Q and 1Q#;

a signal control module which includes a chip SN74HC74 and its peripheral circuit, and which can convert the high-frequency digital signal to a high-frequency digital signal having the same duty cycle as the PWM signal, wherein the PWM signal, the posterior stage interference of which is reduced by using the inverting function of the posterior stage interference reduction module, is inputted into the signal control module so as to control the width of two narrow pulses, and thereby to adjust the duty cycle of the high-frequency signals 1Q and 1Q#;

a signal delay module which includes a chip DS1013 and its peripheral circuit, and which can delay and output the high-frequency signals 1Q and 1Q#, the posterior stage interference of which is reduced by the posterior stage interference reduction module twice, so as to obtain two high-frequency signals which differ from each other by half a cycle;

a signal computation module which includes a chip 74HC08 and its peripheral circuit, and which can make an "AND" operation on the following signals so as to produce four signals: (1) two high-frequency signals which differ from each other by half a cycle, (2) a signal from positive power source, and (3) the PWM signals outputted by the signal control module and the high-frequency digital signals having the same duty cycle as the PWM signals; and a signal amplification and transmission module, which includes a chip IXDD414 and its peripheral circuit, and which can amplifies the four signals and output the amplified four signals to an ultrasonic transmitting apparatus.

When the ultrasonic fat reduction and body shaping machine of this invention is used, operations can be selected according to the menu on the touch screen 6, and the lift cylinder body can be controlled to make up-and-down movement via the button 7.

The invention claimed is:

1. An ultrasonic fat reduction and body shaping machine, characterized in that, the ultrasonic fat reduction and body shaping machine comprises a treatment head, a wave source carrying apparatus, a mechanical arm, a treatment bed-top, a lift cylinder body, a treatment bed-base, a touch screen, a button and control circuits; a menu for user selection operation is provided on the touch screen; the button is a switch for controlling up-and-down movement of the lift cylinder body; the treatment head is selectively clamped in the wave source carrying apparatus and they both as a whole part are fixedly connected to the mechanical arm; the mechanical arm is fixedly connected to the lift cylinder body which is fastened on the treatment bed-base; and the main frame of the treatment bed-top is welded by metal pipes; two groups of guide track-slider mechanisms and displacement driving mechanisms are provided along a length direction and a width direction of the treatment bed-top, respectively; each group of the guide track-slider mechanisms has two guide tracks parallel to each other, and the two groups of the guide track-slider mechanisms are superposed orthogonally in direction; the treatment bed-base is a supporting structure welded by metal pipes; the control circuit for controlling the ultrasonic fat reduction and body shaping machine is installed between the treatment bed-top and the treatment bed-base; the displacement driving mechanism is an electric motor displacement driving mechanism.

2. The ultrasonic fat reduction and body shaping machine according to claim 1, characterized in that, the main part of the treatment head is configured as a self-focusing spherical ultrasonic transducer, the internal structure of the treatment head further includes an ultrasonic transmission medium container and a circulating water cooling system; and the external structure of the main part of the treatment head includes a handle for the treatment head and an adapter.

3. The ultrasonic fat reduction and body shaping machine according to claim 1, characterized in that, the mechanical arm includes hold parts a mounting seat for the treatment head, parallelogram connecting rods, a locking member, a rotary shaft, and air springs; the hold parts, each in a rod shape, are located one at each side of the mounting seat for the treatment head respectively and movably connected thereto; the mounting seat for the treatment head is a connector for the mechanical arm and the wave source carrying apparatus; one side of the mounting seat for the treatment head is fixedly connected to the parallelogram connecting rods and the other side of which is fixedly connected to the wave source carrying apparatus; there are two groups of parallelogram connecting rods that are connected together via a trapezoidal connector; one group of the parallelogram connecting rods is connected at one end to the trapezoidal connector via the rotary shaft, and fixedly connected at the other end to the mounting seat for the treatment head; the other group of the parallelogram connecting rods is fixedly connected at one end to the trapezoidal connector, and connected at the other end to a triangular active connector via the rotary shaft; the parallelogram connecting rods can rotate freely about the rotary shaft; there are two air springs; one of the air springs is connected at one end to the trapezoidal connector via the rotary shaft, and connected at the other end with the locking member and fixedly connected to the mounting seat for the treatment head; this air spring is connected to the hold parts via a metal wire; the other air spring is connected at one end with the locking member and fixedly connected to the trapezoidal connector, and connected at the other end to the triangular connector via the rotary shaft.

4. The ultrasonic fat reduction and body shaping machine according to claim 1, characterized in that, the lift cylinder body includes an electric motor, a feed rod, a means for locking and a mechanical arm bracket; the feed rod is a rod-shaped structure with high surface smoothness; the means for locking has a central hole for the feed rod to be socketed thereinto; the mechanical arm bracket is a platform parallel to the ground; the feed rod and the means for locking are socketed together and fixedly connected with each other; the lift cylinder body is fixedly connected to the means for locking in a locking manner and fixedly connected to the supporting structure of the treatment bed-base by means of the feed rod and the means for locking; inside the lift cylinder body is provided with a lift rod.

5. The ultrasonic fat reduction and body shaping machine according to claim 1, characterized in that, the control circuit for the treatment head includes the following modules:

a signal generation module which includes a chip AD9834 and its peripheral circuit, and which can produce a high-frequency sine wave signal by inputting data at a control terminal of the signal generation module;

a signal conversion module which includes a chip MAX913 and its peripheral circuit, and which can convert the high-frequency sine wave signal to a high-frequency digital signal;

a posterior stage interference reduction module which includes a chip 74HC04 and its peripheral circuit, and which can reduce the posterior stage interference of the following signals by using inversion cancellation means: the high-frequency digital signal, a PWM signal and high-frequency signals 1Q and 1Q#;

a signal control module which includes a chip SN74HC74 and its peripheral circuit, and which can convert the high-frequency digital signal to a high-frequency digital signal having the same duty cycle as the PWM signal, wherein the PWM signal, the posterior stage interference of which is reduced by using the inverting function of the posterior stage interference reduction module, is inputted into the signal control module so as to control the width of two narrow pulses, and thereby to adjust the duty cycle of the high-frequency signals 1Q and 1Q#;

a signal delay module which includes a chip DS1013 and its peripheral circuit, and which can delay and output the high-frequency signals 1Q and 1Q#, the posterior stage interference of which is reduced by the posterior stage interference reduction module twice, so as to obtain two high-frequency signals which differ from each other by half a cycle;

a signal computation module which includes a chip 74HC08 and its peripheral circuit, and which can make an "AND" operation on the following signals so as to produce four signals: (1) two high-frequency signals which differ from each other by half a cycle, (2) a signal from positive power source, and (3) the PWM signals outputted by the signal control module and the high-frequency digital signals having the same duty cycle as the PWM signals; and a signal amplification and transmission module, which includes a chip IXDD414 and its peripheral circuit, and which can amplifies the four signals and output the amplified four signals to an ultrasonic transmitting apparatus.

* * * * *